United States Patent [19]

Hohorst

[11] Patent Number: 4,974,453
[45] Date of Patent: Dec. 4, 1990

[54] METHOD AND APPARATUS FOR NITROGEN OXIDE DETERMINATION

[75] Inventor: Frederick A. Hohorst, Idaho Falls, Id.

[73] Assignee: United States Department of Energy, Washington, D.C.

[21] Appl. No.: 424,028

[22] Filed: Oct. 19, 1989

[51] Int. Cl.$^5$ .............................................. G01N 1/00
[52] U.S. Cl. .............................. 73/863.11; 73/864.81
[58] Field of Search .............. 73/1 G, 863.11, 863.81, 73/863.83, 863.86, 864.34, 864.81

[56] References Cited

U.S. PATENT DOCUMENTS

| | | | |
|---|---|---|---|
| 3,960,500 | 6/1976 | Ross et al. | 73/863.11 |
| 4,008,620 | 2/1977 | Narato et al. | 73/864.34 |
| 4,094,187 | 6/1978 | Navarre, Jr. | 73/864.34 |
| 4,101,282 | 7/1978 | Ririe | 73/1 G |
| 4,134,289 | 1/1979 | Bohl et al. | 73/864.34 |
| 4,456,014 | 6/1984 | Buck et al. | 73/863.86 |
| 4,485,684 | 12/1984 | Weber et al. | 73/863.11 |
| 4,597,285 | 7/1986 | Kuchar et al. | 73/1 G |
| 4,854,180 | 8/1989 | Mauleon et al. | 73/863.86 |

Primary Examiner—Robert Raevis
Attorney, Agent, or Firm—Mark P. Dvorscak; Robert J. Fisher; William R. Moser

[57] ABSTRACT

Method and apparatus for determining nitrogen oxide content in a high temperature process gas, which involves withdrawing a sample portion of a high temperature gas containing nitrogen oxide from a source to be analyzed. The sample portion is passed through a restrictive flow conduit, which may be a capillary or a restriction orifice. The restrictive flow conduit is heated to a temperature sufficient to maintain the flowing sample portion at an elevated temperature at least as great as the temperature of the high temperature gas source, to thereby provide that deposition of ammonium nitrate within the restrictive flow conduit cannot occur. The sample portion is then drawn into an aspirator device. A heated motive gas is passed to the aspirator device at a temperature at least as great as the temperature of the high temperature gas source. The motive gas is passed through the nozzle of the aspirator device under conditions sufficient to aspirate the heated sample portion through the restrictive flow conduit and produce a mixture of the sample portion in the motive gas at a dilution of the sample portion sufficient to provide that deposition of ammonium nitrate from the mixture cannot occur at reduced temperature. A portion of the cooled dilute mixture is then passed to analytical means capable of detecting nitric oxide.

30 Claims, 1 Drawing Sheet

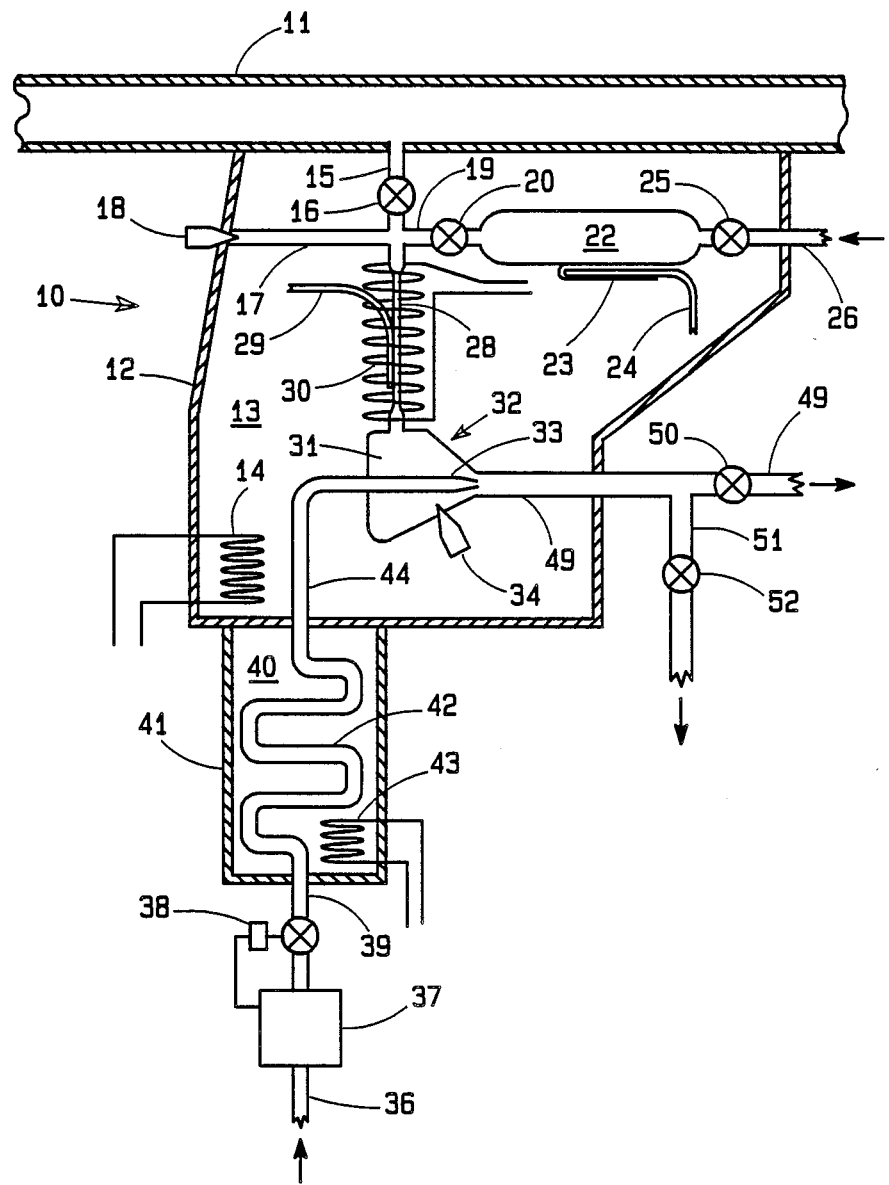

METHOD AND APPARATUS FOR NITROGEN OXIDE DETERMINATION

CONTRACTUAL ORIGIN OF THE INVENTION

The United States Government has rights to this invention pursuant to Contract No. DE-AC07-84ID12435 between the U.S. Department of Energy and Westinghouse Electric Corporation.

BACKGROUND OF THE INVENTION

The present invention relates to method and apparatus for determination of nitrogen oxide. In particular this invention relates to method and apparatus for determination of nitrogen oxide in a high temperature gas stream.

Nitrogen oxides ($NO_x$) are regulated by governmental agencies because they constitute a health risk. To satisfy these regulations, numerous processes for the removal or destruction of nitrogen oxides have been devised. Some processes utilize the reaction of nitrogen oxides with ammonia at elevated temperatures, either with a catalyst or without a catalyst. Under proper conditions, these reactants yield nitrogen and gaseous water nearly quantitatively.

Control of nitrogen oxide removal or destruction processes in an efficient, economical, and safe manner requires continuous monitoring of the concentrations of several species, including specifically nitric oxide, nitrogen dioxide, and ammonia, in the presence of nitrogen, oxygen, ammonium nitrate, nitric acid, and water, among other gaseous species. Conventional methods of analysis of these species, including chemical analysis of grab samples and instrumental on-line monitoring, are too time consuming and/or can only be performed at near room temperature. At such temperatures, deposition of ammonium nitrate can occur in transport lines or sample vessels, thereby causing low analytical results.

Accordingly, it is an object of the present invention to provide a method and apparatus for the determination of nitrogen oxide in a gas sample which yields analytical results having improved accuracy.

It is another object of the present invention to provide a method and apparatus for the determination of nitrogen oxide in a high temperature gas stream with improved accuracy.

These and other objects of the present invention, as well as the advantages thereof, will become more clear from the description which follows.

SUMMARY OF THE INVENTION

These objects are achieved by extracting a sample portion of a high temperature gas source and passing the sample portion at the high temperature to an aspirator device using an air or nitrogen jet discharging from the aspirator nozzle to control, and in fact eliminate, the deposition of ammonium nitrate by dilution of the sample portion before cooling the sample for on-line analysis.

Accordingly, in its method aspects of the present invention comprehends a method for determining nitrogen oxide content in a high temperature process gas, which involves withdrawing a sample portion of a high temperature gas containing nitrogen oxide from a high temperature gas source to be analyzed. The withdrawn sample portion is passed through a restrictive flow conduit, which may be a capillary or a restriction orifice, or the like. The restrictive flow conduit is heated to a temperature sufficient to maintain the sample portion flowing through the restrictive flow conduit at an elevated temperature at least as great as the temperature of the high temperature gas source, to thereby provide that deposition of ammonium nitrate within the restrictive flow conduit cannot occur. The sample portion is then drawn from the restrictive flow conduit to the suction side of an aspirator device. A heated motive gas is passed to the aspirator device at a temperature at least as great as the temperature of the high temperature gas source. The motive gas is passed through the nozzle of the aspirator device under conditions sufficient to aspirate the heated sample portion through the restrictive flow conduit and produce a mixture of the sample portion in the motive gas at a dilution of the sample portion sufficient to provide that deposition of ammonium nitrate from the mixture cannot occur at reduced temperatures, such temperatures being as low as the ambient temperature or even lower. At least a portion of the cooled dilute mixture is then passed to analytical means which is preferably capable of detecting nitric oxide levels down to at least 2 ppb.

In its method aspects the present invention also involves a method for the calibration of the restrictive flow conduit so that the degree of dilution of the sample portion of the high temperature gas source in the motive gas may be determined.

In its apparatus aspects the present invention comprehends a fluid sampling apparatus, suitable for sampling a high temperature process gas for measurement of nitrogen oxides, which contains an inlet conduit including means for connection to a high temperature gas source to be sampled. The inlet conduit is connected to an aspirator device by means of a restrictive flow conduit. The aspirator device has a suction inlet opening, a motive gas inlet opening, and an exit opening for discharging a gas mixture of motive gas and sample gas. A motive gas inlet conduit is in fluid communication with the motive gas inlet opening of the aspirator and the motive gas inlet conduit includes means for connection to a source of high pressure motive gas, which typically may be air or nitrogen. A first heating means is located at the restrictive flow conduit. The first heating means has the capacity to maintain a gas sample passing through the restrictive flow conduit at a temperature not less than the high temperature of the gas source. A second heating means is located at the motive gas inlet conduit for heating the motive gas up to a temperature not less than the high temperature of the gas source. A discharge conduit is in fluid communication with the aspirator for transmitting a mixture of the motive gas and the sample portion of the high temperature gas source as a diluted mixture of the sample portion.

A clearer understanding of the present invention will be obtained from the disclosure which follows when read in light of the accompanying drawing.

BRIEF DESCRIPTION OF THE DRAWINGS

The Drawing Figure is a simplified schematic representation of an embodiment of the inventive apparatus.

DESCRIPTION OF THE PREFERRED EMBODIMENTS

Referring now to the Drawing Figure there is shown a fluid sampling apparatus 10 in accordance with the present invention. The fluid sampling apparatus is mounted adjacent to a fluid conduit 11 which contains a fluid to be sampled. Conduit 11 may be a high temperature flue gas line or a high temperature process line, containing a gas having an unknown amount of nitrogen oxides. An insulated housing 12 encompasses the sampling apparatus 10 to define a heated chamber 13. The chamber 13 contains a chamber heater 14 which is shown as an electrical resistance heater.

A sample withdrawal line 15 is conventionally connected to the process conduit 11. A valve 16 is located in the sample withdrawal line 15. The sample withdrawal line branches into a cross connection which contains a left-hand line 17 terminating in a pressure transducer 18, and a right-hand line 19 terminating in a valve 20. On the right-hand side of the valve 20 is a calibration cylinder 22. The calibration cylinder 22 has a thermometer well 23 containing a temperature sensor, such as a thermocouple 24. The thermometer well is welded to the outside surface of the cylinder 22. A valve 25 on the right-hand side of the cylinder 22 connects the calibration cylinder to an inlet line 26 by means of which a calibration gas may be admitted to the calibration cylinder.

The lower portion of the cross connection passes to a restrictive flow conduit 28, which for purposes of illustration is shown to be a capillary tube. However, the restrictive flow conduit 28 may be a standard size conduit including a restriction orifice or any similar device which restricts the flow of a sample gas. A temperature sensor 29, such as a thermocouple, is taped to the outside of the capillary tube. An electrical resistance heater 30 encompasses the capillary tube and the temperature sensor 29. The capillary tube 28 passes a sample of gas from conduit 11 to the suction chamber 31 of an aspirator device 32. The aspirator device contains a jet nozzle 33. In addition, the aspirator device may contain a pressure transducer 34 which senses the vacuum which is imposed within the aspirator suction chamber 31 by a motive gas passing through the nozzle 33.

Motive gas for use in operating the aspirator 32 is introduced into the apparatus by means of an input gas line 36. The motive gas may be air or it may be an inert gas such as nitrogen. The motive gas is passed via line 36 into a flow controller 37 which may be a mass flow controller. The flow controller 37 sends a signal to the flow control valve 38 in order to control the amount of motive gas passing through the aspirator nozzle 33, to thereby control the amount of dilution of a sample passing into the suction chamber 31 from the restrictive flow conduit or capillary 28. The motive gas is passed from the flow control valve 38 via line 39 to a preheating chamber 40 contained within a preheating chamber housing 41. The preheating chamber 40 contains a preheating coil 42 for the motive gas and a heating element 43 which is shown as an electrical resistance heater. A hot gas line 44 leaves the preheating chamber 40 and passes into the aspirator 32 where it terminates in the nozzle 33.

An aspirator discharge line 49 conveys a mixture of the gas sample from the capillary 28 and the motive gas away from the aspirator. A valve 50 is contained in the aspirator discharge line 49. A line 51 conveys a portion of the discharged mixture of sample gas and motive gas via a valve 52 to a conventional nitrogen oxide analyzer, not shown, as well as to other analyzers to the extent desired.

The sample of gas which is withdrawn from the conduit 11 by means of the aspirator 32 via the capillary 28, is quantitatively diluted with the nitrogen motive gas while the temperature of the process stream of conduit 11 is greater than 210° C. The sample of gas withdrawn from the capillary and the motive gas passed into the aspirator, as well as the temperature within chamber 13, are also maintained above 210° C. This dilution may initially be greater than 1,000,000,000. (Dilution is defined as the ratio of the motive gas to the sample of gas to be analyzed.) This dilution serves three purposes. It substantially decreases further reaction of nitrogen oxides with oxygen, it minimizes the potential for immediate formation of ammonium nitrate, and it lowers the concentration of water in the diluted sample, thus minimizing the possibility of moisture condensation when the temperature of the diluted sample is lowered.

The heated capillary 28 which controls the flow of the sample from the process line 11, assures that highly diluted samples of the process gas may be obtained by using this invention. Such highly diluted samples usually have slower reactions rates between the various components contained therein than are experienced at the original concentrations. Dilutions are variable and may be in excess of 1,000,000,000. The heated restrictive flow conduit, such as the capillary 28, assures a constant flow of sample gas because it is at a constant temperature not less than the maximum process gas temperature at the location were the sample is to be measured. A submicron filter may be used to protect this restrictive flow conduit (capillary 28) from particulate matter, such as fly ash contained in a hot flue gas.

The transducer 18 measures the pressure in the sample lines 15, 17 and 19 and the transducer 34 measures the pressure in the vacuum chamber 31 of the aspirator 32. This allows calibration of the flow rate through the capillary versus the measured pressure difference at the temperature being used. The mass flow controller 37 also meters the motive gas, thus measuring the flow rate of the nitrogen or air passing to the aspirator These data allow calculation of the dilution of the process stream sample so that the measured concentrations of components in the diluted stream from the aspirator may be related to the actual concentrations in the process stream contained in conduit 11.

The heating units of the apparatus are sufficient for maintaining the temperature of the capillary not lower than the temperature of the process stream in conduit 11. Additionally, the two chamber heaters maintain the temperature of the motive gas not lower than the temperature of the process stream in conduit 11. The heaters further provide heating sufficient to preheat the motive gas entering the aspirator to compensate for the cooling effect of the expansion which occurs as it passes through the aspirator nozzle 33. Additionally, reserved heating capability is provided sufficient to raise the temperature of the aspirator and the capillary more than 100° C. above normal operating temperature, if desired, as a way of decomposing or clearing any actual or suspected plugs without the necessity of cooling the inventive apparatus or performing hands-on maintenance.

Valving is also provided which is capable of reversing the flow through the capillary as a way of clearing any actual or suspected plugs without the necessity of cooling the inventive apparatus to ambient temperature and performing hands-on maintenance. This is accomplished by closing off the valves 50 and 52 of the discharge lines. This causes motive gas to back up through the suction chamber 31 of the aspirator and pass out through the capillary 28 and into the process conduit 11, thereby clearing any particulate matter which may have been deposited in the capillary.

It is to be noted that during the experimental work with the inventive apparatus, no plugging has been experienced in the capillary. Accordingly, it has not been necessary to increase the temperature at the capillary or to reverse the flow of the motive gas through the capillary in order to clear out any suspected plugs of ammonium nitrate.

The components of the inventive apparatus are manufactured from materials which are selected to be capable of withstanding the environment of the use. Typically, stainless steels of the 300 Series are utilized. These stainless steels are capable of withstanding temperatures greater than 400° C. and pressures greater than 20 atmospheres.

The small portion of the diluted mixture containing the sample gas in the motive gas which is drawn off via line 51 is cooled to a temperature conducive to the analysis to be undertaken. The analysis is rapid, conventional, and on-line by means of a detection device, such as a chemiluminescence detection device, which is capable of measurements down to less than or equal to 2 ppb of nitric oxide. Conventional on-line measurement of oxygen and water in the diluted sample may also be performed by using known techniques and conventional apparatus.

Selective conversion of nitric acid, nitrogen dioxide, and/or ammonia to nitric oxide using known technology allows determination of the sum of nitric oxide plus nitric acid plus nitrogen dioxide plus ammonia. Samples are analyzed for nitric oxide by the chemiluminescence detection device as previously noted. Concentrations of the individual compounds are subsequently determined by difference.

Measurement of nitric oxide, or compounds which have been converted to nitric oxide, is started at 1,000,000,000 to 1 dilution. If concentrations are below detection limits, then the detection limits are used in the appropriate equilibrium equations. Otherwise, the experimental concentrations are used in the following equations:

$$NH_4NO_3(s) \rightleftharpoons NH_3 + HNO_3$$

$$K_1 = [NH_3] \times [HNO_3]/[NH_4NO_3(s)]$$

or $$K_1 = [NH_3] \times [HNO_3]$$

$$2 HNO_3 \rightleftharpoons 2 NO_2 + H_2O + 0.5 O_2$$

and $$K_2 = [NO_2]^2 \times [H_2O] \times [O_2]^{0.5}/[HNO_3]^2$$

These equations may be handled more conveniently by rearrangement to the form:

$$K_3 = K_1 K_2^{0.5} = [NH_3] \times [NO_2] \times [H_2O]^{0.5} \times [O_2]^{0.25}$$

These equations are equilibrium equations. They state nothing regarding the rates of the reactions being considered. The significance of applying these equations is that no consideration need be given to reaction rates. So long as the equilibrium constant, $K_1$, is not exceeded, no ammonium nitrate in excess of that permitted by equilibrium can form regardless of rate. Therefore, none can be deposited in the equipment.

As concentrations increase and their product approaches the equilibrium constant, the nitrogen flow to the aspirator can be increased, thereby further diluting the sample and preventing deposition of ammonium nitrate in the lower temperature portions of the system. Thus, the flow of nitrogen motive gas may be adjusted upward or downward in order to assure that the dilution will be sufficient to prevent precipitation of ammonium nitrate from the diluted mixture of sample gas in motive gas, while also assuring that the chemiluminescence detection device can detect nitrogen oxide in the dilute mixture.

Values of the equilibrium constants are greatly dependent on the temperature of the measurement. The theoretical value of $K_1$, for example, equals 11 $ppb^2$ at 20° C.; 1,400 at 40° C.; 95,000 at 60° C.; 3,900,000 at 80° C.; and 140,000,000 at 100° C. Chemiluminescence detection devices, capable of measurements down to less than or equal to 2 parts per billion of nitric oxide, can routinely operate at 40° C. In simplest terms, at 40° C. the product of the ammonia concentration in ppb times the nitric acid concentration in ppb must exceed 1400 $ppb^2$ in order for any solid ammonium nitrate to deposit. Even a modest increase in operating temperature of the detection device can result in large improvements in the measuring range of the system, as may be seen from the rapidly increasing values of $K_1$ at increasing temperatures, as indicated hereinabove by the values for $K_1$ given at the different temperatures.

In the above process for controlling the deposition of ammonium nitrate, a useful approximation in some situations is to consider the nitric acid concentration as less than or equal to the sum of nitric oxide plus nitric acid plus nitrogen dioxide. This permits more rapid evaluation of concentration and easier comparison of them with the equilibrium constant.

The measured concentrations of nitric oxide, nitrogen dioxide, and ammonia in the diluted sample are multiplied by the dilution factor in order to calculate the concentration in the process gases before dilution. The large initial dilutions slow subsequent reaction of these species with oxygen by more than two orders of magnitude. Therefore, the measured values are very nearly equal to the concentrations in the process gases at the time of dilution. Response time will vary depending on the physical locations of components, but it can easily be less than 60 seconds.

The electrical outputs from these measurements are voltages which can be converted to signals which can control the measurement system, or the process system being sampled, or both.

EXAMPLE A

A system was constructed to generate high concentrations of nitrogen oxides or ammonia, or both, at elevated temperatures in the following manner:

Oxygen and nitric oxide were mixed and admitted to a delay volume which permitted reaction to form some nitrogen dioxide. This mixture was further diluted with nitrogen and heated to the desired temperature range, thereby producing a mixture of nitrogen oxides, oxygen, and nitrogen. An alternative was to pump aqueous nitric acid solution into the system with additional heating to vaporize all of the liquid, thereby producing a mixture of nitrogen oxides/nitric acid, gaseous water, oxygen, and nitrogen. Gases were measured by calibrated mass flowmeters. Liquids were measured by mass changes. Capillaries were calibrated in-situ as described below. Temperatures were measured by thermometers or thermocouples and could be altered by changing the voltages being applied to the resistance heaters. Ammonia was measured using a mass flowmeter and added to the preceding mixtures while maintaining the temperature between 220 and 300° C.

Capillaries were constructed of stainless steel, although they could, of course, be made of any convenient, nonreactive metal or nonmetal. The following is a typical fabrication example. Cajon brand VCR fittings were LASER welded onto a 60.64 cm length of 1/16 inch OD tubing whose bore diameter was a nominal 0.010 inch. For aspiration the capillary was attached to a Fox Valve Development Corp. Model 410-VCR MiniEductor (i.e., "air jet") designed for operation at a motive pressure of 60 to 100 psig and a motive flow of 1 to 1.5 SCFM. Under these operating conditions, the absolute pressure in the suction arm of the air jet aspirator is less than 100 torr. All connections to the air jet aspirator were made through VCR fittings welded to the air jet. Provision was made so that a filter gasket containing a 0.5 micron stainless steel filter could be added to protect the capillary tubing from plugging.

For calibration, a convenient length of copper tubing was attached through fittings to the capillary tubing, instead of the line to be sampled, and all were heated to the desired temperature. The copper tubing facilitated preheating of the air entering the capillary. A calibrated bubble meter was then attached to the copper tubing and the rate of movement of a soap bubble was timed with a stopwatch. Table 1 gives results of the calibration of this capillary using the mean of five or ten determinations.

TABLE 1

| Configuration | Calibration Of A Capillary | | |
|---|---|---|---|
| | Temperature (°C.) | Flow Rate (ncc/min)* | 95% C.I.** (ncc/min) |
| 60.64 cm Plain (No filters) | 22.1 ± 0.2 | 12.407 | 0.030 |
| | 231. ± 2 | 5.149 | 0.039 |
| 60.64 cm with 2–0.5 micron | 22.2 ± 0.2 | 8.186 | 0.039 |
| | 234. ± 2 | 3.746 | 0.015 |

TABLE 1-continued

| Configuration | Calibration Of A Capillary | | |
|---|---|---|---|
| | Temperature (°C.) | Flow Rate (ncc/min)* | 95% C.I.** (ncc/min) |
| Filters | | | |

*ncc denotes normal cubic centimeters, i.e., 21° C. and 760 torr.
** Confidence Interval The accuracy and the utility of this invention is illustrated by the following Examples A1, A2, A2.1, A2.2, A2.3 and A2.4.

EXAMPLE A1

An unfiltered capillary such as previously described was installed and operated at 231 ±2° C. The flow rate through the capillary at this temperature was 5.15 ncc/min when operating between 640 torr and 100 torr. (ncc/min denotes normal cubic centimeters, i.e., 21° C. and 760 torr, per minute.) The resulting dilution under these conditions is about 6500 fold. The calibration of the chemiluminescence monitor was independently verified by checking it against a nitrogen dioxide permeation tube certified by the manufacturer to have an accuracy of ±5% and to be traceable to NBS standards. The average response of the system was 0.987 with a 95% confidence limit of ±0.054 as derived from the data in Table 2. These data document the applicability of this technique to the accurate dilution of gase at high temperatures.

EXAMPLE A2

A filtered capillary such as previously described was installed which had a flow rate of about 3.5 ncc/min at 270° C. The capillary ran from the line to be sampled to an air jet operated at about 70 psig air and at a flow rate of about 33 nL/min. (nL/min denotes normal liters, i.e., 21° C. and 760 torr, per minute.)

TABLE 2

| | | | Response of Monitor to Diluted Samples | | | | |
|---|---|---|---|---|---|---|---|
| Time (Min) | NO (nccm) | Total Flow (nLm) | System Calc $NO_x$ (ppm) | Jet (nLm) | Monitor Obs $NO_x$ (ppm) | System Obs $NO_x$ (ppm) | System Response (Obs/Calc) |
| 33 | 100 | 14.3 | 6970 | 33.8 | 1.100 | 7220 | 1.036 |
| 38 | 100 | 14.3 | 6970 | 33.1 | 1.070 | 6880 | 0.987 |
| 43 | 100 | 43.8 | 2280 | 33.4 | 0.379 | 2460 | 1.079 |
| 48 | 100 | 43.8 | 2280 | 33.2 | 0.349 | 2250 | 0.987 |
| 53 | 100 | 85.0 | 1180 | 33.0 | 0.185 | 1190 | 1.008 |
| 63 | 100 | 85.1 | 1180 | 33.1 | 0.167 | 1070 | 0.907 |
| 71 | 100 | 11.7 | 8540 | 33.6 | 1.180 | 7700 | 0.902 |
| 76 | 100 | 11.7 | 8540 | 33.7 | 1.180 | 7720 | 0.904 |
| 81 | — | 11.6 | — | 33.4 | 0.050 | 320 | — |
| 86 | — | — | — | — | 0.011 | — | — |
| | | | Mean of 8 | 33.36 | | | 0.9865 |
| | | | s | 0.31 | | | 0.0646 |
| | | | s (%) | 0.9 | | | 6.5 | nccm = normal cubic centimeters per minute
nLm = normal liters per minute
ppm = parts per million by volume
Calc = calculated
Obs = observed The resulting dilution was about 9400 fold. Subsequent sampling of the effluent from the air jet with a chemiluminescence nitrogen oxides monitor afforded a convenient method of monitoring the gas streams containing the equivalent of 100 to 30,000 ppm $NO/NO_2/NO_x/HNO_3$.

The following Examples A2.1 through A2.4 serve to illustrate the utility of this procedure in analyzing gas samples which are difficult to analyze on-line by conventional methods.

EXAMPLE A2.1

A further demonstration of the utility of the invention was made by pumping a dilute liquid solution of nitric acid (about 1.5 M) into the system while increasing the heater voltage to assure complete volatilization of the solution. In this way, a gas mixture with a dew point of about 80.3° C. was prepared having the calculated composition reported in Table 3.

The test stream described in Table 3 is somewhat more difficult to maintain under steady state conditions because of the need to volatilize all of the liquid. Furthermore, the total of $NO_x/HNO_3$ is specified, although the degree of decomposition of nitric acid under these conditions is unknown. The converter in the monitor Labs Model 8840 chemiluminescence monitor does not differentiate between $NO_x$ and $HNO_3$, since both species are converted to NO and detected by the monitor. (Filters are reported in the literature which

TABLE 3

| Calculated Composition of High Dew Point Gas Stream | | | |
|---|---|---|---|
| Component | Flow Rate (ncc/min) | Composition (%) | Partial Pressure (torr) |
| Argon | 46 | 0.36 | 2.3 |
| $NO_x/HNO_3$ | 203 | 1.59 | 10.3 |
| Oxygen | 1516 | 11.90 | 76.6 |
| Nitrogen | 3853 | 30.24 | 194.7 |
| Water (g) | 7124 | 55.91 | 359.9 |
| TOTAL | 12,742 | 100.00 | 643.8 |

(filters are reported in the literature which selectively adsorb $HNO_3$, thereby making it possible to determine the individual concentrations by difference).

Even with these added difficulties, this example of the use of the invention is very informative because it approximates a situation often encountered, namely, the sampling of very moist gas streams containing nitrogen oxides or nitric acid or both. In this example, dilute nitric acid was pumped into the system over a period of 142 minutes, thereby generating a mixture with an average $NO_x/HNO_3$ concentration of 15,900 ppm. The invention was operated at 52±2° C. at which temperature it had a flow rate of 3.65 ncc/min. After reaching apparent equilibrium, the observed $NO_x/HNO_3$ concentration for the system was 16,500 to 16,900 ppm. The output of the chemiluminescence monitor went to a strip chart recorder. The integrated response of the monitor to $NO_x/HNO_3$ over the duration of the experiment was 1.11 or 11% higher than theoretical.

EXAMPLE A2.2

Nitric oxide, oxygen, and nitrogen gases were combined to give a calculated $NO_x$ concentration of about 20,000 ppm. The outputs of various mass flowmeters, mass flow controllers, thermocouples, and the chemiluminescence monitor were connected to a Hewlett Packard data acquisition system which could be programmed to monitor all outputs at convenient intervals.

Direct measurement of the $No_x$ concentration using the invention described hereinabove with a chemiluminescence monitor gave a mean value of 18,200 ppm (9.6% lower than the calculated makeup value). Addition of ammonia to a calculated level of 8800 ppm reduced the apparent $NO_x$ concentration by 3990 ±182 ppm. Increasing the ammonia to 17,000 ppm reduced the apparent $NO_x$ concentration by 6920 ±226 ppm. Increasing the ammonia still further to 33,300 ppm reduced the apparent $NO_x$ concentration by 11,900±694 ppm. Stopping the ammonia low increased the $NO_x$ concentration to 19,300 ppm (6.7% lower than the calculated makeup value).

These data are summarized in Table 4 which reports means and 95% confidence limits for those means. Means at the beginning and end of the experiment are calculated from 8 individual values. Means during addition of ammonia are calculated from 4 individual values taken at 5 minute intervals during each 30 minute run. The first and last value were discarded because equilibrium may not yet have been attained. The decrease in the apparent $NO_x$ concentration corresponds to 36 to 45% of the ammonia concentration.

The NO concentration shows changes which may or may not prove significant. There is an inference that the increase in NO concentration was due to oxidation of $NH_3$. Alternatively, there may have been a reaction of $NO_x$ with $NH_3$ to produce nitrogen and water among other possible products. However, additional extensive work would be required to confirm whether, in fact, such oxidation actually occurs.

TABLE 4

| Addition of Ammonia to Nitrogen Oxides | | | | | |
|---|---|---|---|---|---|
| | | Calculated Mean | | Observed Mean | |
| Time (min) | Total Flow (ncc/min) | $NH_3$ (ppm) | $NO_x$ (ppm) | NO (ppm) | $NO_x$ (ppm) |
| 30 | 4640 ± 33 | — | 20100 ± 188 | 1040 ± 107 | 18200 ± 190 |
| 48 | Start $NH_3$ at 8800 ppm | | | | |
| 65 | 4640 ± 37 | 8800 ± 45 | 20000 ± 142 | 1490 ± 36 | 16000 ± 114 |
| 78 | Increase $NH_3$ to 17,000 ppm | | | | |
| 95 | 4580 ± 37 | 17000 ± 76 | 20200 ± 128 | 1620 ± 253 | 1330 ± 186 |
| 108 | Increase $NH_3$ to 33,300 ppm | | | | |
| 125 | 4550 ± 44 | 33300 ± 348 | 20400 ± 212 | 3930 ± 2150 | 8490 ± 661 |
| 138 | Stop $NH_3$ | | | | |
| 160 | 4480 ± 175 | — | 20700 ± 793 | 2480 ± 688 | 19300 ± 2490 |

EXAMPLE A2.3

Nitric acid, oxygen, and nitrogen were combined to give a calculated $NO_x$ concentration of 18,000 ppm with a calculated dew point of 83–85° C. Ammonia was added to give a calculated concentration of 3400 ppm. The observed $NO_x$ concentration was 9700 ppm. When ammonia addition was stopped, the observed $NO_x$ concentration increased to 15,000 ppm. Thus, the inventive apparatus has utility for determining $NO_x$ concentrations for these general conditions.

EXAMPLE A2.4

After extended use of the apparatus, which included recent exposures to nitric oxide, nitrogen dioxide, and nitric acid, a purge of only nitrogen and oxygen was initiated at temperatures above 240° C. The observed $NO_x$ concentration fell to 600 ppm and the concurrent nitric oxide concentration fell to 70 ppm. Introduction of ammonia at a calculated concentration of 31,000 to 35,000 ppm resulted in generation of nitric oxide at levels of 1600 to 5300 ppm over a period of 50 minutes. After 120 minutes, the nitric oxide concentration had fallen to 160 ppm and the $NO_x$ concentration had fallen to 720 ppm. This run leads to the conclusion that nitrogen compounds of some type had accumulated in the system and that they were released by the introduction of ammonia.

The application of equilibrium constants to these types of measurements necessitates control of the capillary size and the dilution flow. The selection of a capillary and an air jet (aspirator device) define relatively fixed flow ranges which will restrict the overall capabilities of the system. The dilution flow, however, may be readily varied to accommodate specific needs within certain limits which may be controlled manually or by computer feedback. In this way, the deposition of ammonium nitrate with its integral loss of accuracy and potentially hazardous conditions can be avoided.

DESCRIPTION OF PREFERRED CALIBRATION TECHNIQUE

The subject for this aspect of the disclosure concerning the inventive apparatus relates to the use of a known, heated volume of gas to permit calibration of the flow rate in the restrictive flow conduit, such as the capillary 28 of the Drawing Figure, at varying temperatures and pressures under operating conditions. This approach also overcomes any possibility of inaccuracies which could result from fractionation of the sample through a small capillary or orifice because both the standard and the sample pass through the same capillary. Furthermore, because this can be done quickly, typically in less than 20 minutes, the use of this calibration invention is especially useful in process applications where it can provide in-situ verification of the accuracy of the system. The frequency of the calibration depends upon the severity of the process environment, so that management might calibrate the apparatus once per shift or once per day, or more or less frequently as desired or necessary.

As previously noted, the inventive apparatus as illustrated in the Drawing Figure utilizes a capillary 28 to restrict the flow of the sample to a small, known rate. Capillaries and orifices are known to cause fractionation of gases. This effect is proportional to the square root of the ratio of the molecular weights. Hence, it becomes greater as the differences in molecular weights of the species becomes greater. Although theoretical calculations of the magnitude of this effect are possible for known gases, process gases with no fixed composition present formidable task. In addition, the presence of a capillary always presents a potential for plugging which would alter the calibration even when the greatest precautions are being taken.

Measurement of the flow rate in a capillary under its operating conditions (i.e., temperature, pressure, physical condition, etc.) is the best method of identifying the potential problems of plugging. Calibration with a standard which is processed identically to the actual sample is the best method of overcoming the potential problems of fractionation. The solution to both problem conditions is to use a known volume which is connected to the inlet of the capillary in place of the sample and which may be valved in without otherwise changing the system. The calculations are easier if both the known volume and the capillary are at the same temperature, but this condition is not essential. The mechanics of the procedure by which this can be accomplished are described in the following paragraphs.

The configuration of the system is shown in the Figure. The pressure is measured by an absolute pressure transmitter (transducer 18) immediately upstream of the capillary 28. Temperatures are measured by the two thermocouples, one taped to the capillary and the other inserted into the thermometer well 23 which was welded to the outside of the "75 cc" cylinder 22. The nominal 75 cc volume of the cylinder 22 plus the piping between cylinder 22 to the valves 16 and 25, plus line 17 and the piping to the capillary inlet, gave the actual calibration volume of 92.02 cc. Outputs from all three sensors were passed to a Hewlett-Packard Model 3497A Data Acquisition System which could interrogate and record the outputs under either manual or preselected control.

Under normal operation of the inventive apparatus, valve 16 is open and valve 20 is closed so that a sample of the process gas of conduit 11 can pass to the capillary. If an inert calibration gas, such as nitrogen, containing a specie in known amount to be measured by the analyzer, such as NO, is admitted with Valves 16, 20 and 25 open, a small portion will be drawn through the capillary while the excess will be vented into the process line 11. This takes but a few minutes and verifies the calibration of the system analyzer, such as the chemiluminescence detection device used in this work, to make certain that the analyzer reads the correct ppb of the active NO component in the calibration gas.

By closing Valve 16, the standard volume can be pressurized to a convenient, desired pressure, P(i), higher than the range of interest. Closing Valve 25 at time zero, t(0), begins a run. The Hewlett-Packard Model 3497A Data Acquisition System can then interrogate and record the sensor outputs at convenient intervals such as 15 or 30 seconds until the pressure falls to some final pressure, P(f), which is still greater than twice the ultimate pressure of the minieductor (the aspirator or air jet).

In summary then, this calibration method invention consists of using a known volume of calibration gas at a convenient operating temperature with an attached absolute pressure transducer and thermocouples as shown schematically in the Figure. The invention is used to calibrate flow rates through flow restrictors such as orifices or capillaries under process conditions. Operation of the calibration invention consists of the following steps:

1. Bringing the capillary 28 and the volume in cylinder 22 to desired operating temperatures for calibration.
2. Closing valve 16.
3. Pressurization of the volume in cylinder 22 and the piping 17 and 19 above the range of interest.
4. Closing the supply valve 25 to initiate a run.
5. Measuring and recording times, pressures, and temperatures as the volume is evacuated from the cylinder 22 and the piping 17 and 19 by the aspirator device 32.

After the above data has been recorded, it is treated in the following way to derive the calibration of the flow restrictor (capillary 28):

1. A multiple regression analysis program is applied to accurately fit the experimental points to an equation.
2. The first derivative of the equation is calculated at pressures for which calibration is desired.
3. The first derivative represents the rate of change of pressure at a specific pressure. Hence, the physical conditions of the system (volume, temperature, coefficient of expansion, etc.) may be applied to convert this derivative to a volume flow rate.

Simulated process conditions in excess of 200° C. and 150 torr (3 psia) were chosen in demonstrating this invention and its operation. Temperature per se is not restrictive as long as it is compatible with the materials of construction and the chosen calibration gas. The ultimate vacuum of the system limits the high pressure side of the flow restrictor (capillary 28) to a minimum of about twice the ultimate vacuum.

The calibration method is illustrated by the following Example B.

EXAMPLE B

The aspirator device, the Mini-Eductor identified in Example A, is capable of attaining a pressure of less than 100 torr absolute even at temperatures above 220° C. The ultimate pressure attained with this experimental configuration and the mini-eductor operating at 1.15 SCFM is about 69.7 torr (1.35 psia) at 230° C. The flow rate through the capillary should therefore be proportional to the upstream pressure squared until the upstream pressure falls to less than 150 torr. Knowledge of the absolute pressure downstream of the capillary (i.e., from pressure transducer 34) is not necessary in the calculations so long as it remains low. The known volume of the calibration cylinder 22 was sized to give a convenient rate of evacuation. If during this evacuation, simultaneous measurements of the time, pressure, and temperature are recorded, data will have been collected in-situ which permit calibration of the capillary for that temperature and at any pressure in the range. A typical example of this data is presented in Table 5.

From these time and pressure data, one can derive equations for the sets of data points over the range of greatest interest by a typical curve fitting technique. For purposes of this disclosure, the range of 380 to 1140 torr (0.5 to 1.5 atm, or 7.3 to 22.0 psia) was arbitrarily chosen.

TABLE 5

| | Raw Data From Run 16* | | |
|---|---|---|---|
| Time (s) | Pressure (mv)** | Capillary Temperature (°C.) | Cylinder Temperature (°C.) |
| 0 | 19.963 | 229.6 | 229.0 |
| 29 | 17.104 | 229.7 | 229.0 |
| 59 | 15.009 | 229.7 | 228.9 |
| 89 | 13.368 | 229.7 | 229.0 |
| 119 | 12.043 | 229.7 | 229.0 |
| 149 | 10.953 | 229.7 | 229.0 |
| 179 | 10.038 | 229.7 | 229.0 |
| 209 | 9.260 | 229.8 | 229.1 |
| 239 | 8.591 | 229.8 | 229.1 |
| 269 | 8.010 | 229.9 | 229.1 |
| 299 | 7.499 | 229.9 | 299.1 |
| 329 | 7.048 | 229.9 | 229.2 |
| 359 | 6.646 | 229.9 | 229.2 |
| 389 | 6.286 | 229.8 | 229.2 |
| 419 | 5.962 | 229.8 | 229.2 |
| 449 | 5.668 | 229.8 | 229.2 |
| 479 | 5.401 | 229.8 | 229.2 |
| 509 | 5.157 | 229.8 | 229.2 |
| 539 | 4.933 | 229.8 | 229.2 |
| 569 | 4.727 | 229.8 | 229.2 |
| 599 | 4.537 | 229.8 | 229.2 |
| 629 | 4.360 | 229.8 | 229.2 |
| 659 | 4.197 | 229.8 | 229.2 |
| 689 | 4.044 | 229.8 | 229.2 |
| 719 | 3.902 | 229.8 | 229.2 |
| 749 | 3.769 | 229.8 | 229.2 |
| 779 | 3.644 | 229.8 | 229.1 |
| 809 | 3.528 | 229.8 | 229.2 |
| 839 | 3.418 | 229.8 | 229.2 |
| 869 | 3.314 | 229.7 | 229.2 |
| 899 | 3.216 | 229.7 | 229.2 |
| 929 | 3.124 | 229.7 | 229.2 |
| 959 | 3.037 | 229.7 | 229.2 |
| 989 | 2.954 | 229.7 | 229.2 |
| 1019 | 2.875 | 229.7 | 229.2 |
| 1049 | 2.801 | 229.7 | 229.2 |
| 1079 | 2.728 | 229.7 | 229.2 |
| 1109 | 2.661 | 229.6 | 229.2 |
| 1139 | 2.596 | 229.6 | 229.2 |
| 1169 | 2.534 | 229.5 | 229.2 |
| 1199 | 2.475 | 229.5 | 229.1 |
| 1229 | 2.419 | 229.5 | 229.1 |
| 1259 | 2.364 | 229.5 | 229.1 |
| 1289 | 2.312 | 229.4 | 229.1 |
| 1319 | 2.263 | 229.4 | 229.1 |
| 1349 | 2.215 | 229.4 | 229.0 |
| 1379 | 2.169 | 229.4 | 229.0 |
| 1409 | 2.125 | 229.4 | 229.0 |
| 1439 | 2.083 | 229.3 | 229.0 |
| 1469 | 2.042 | 229.3 | 228.9 |
| 1499 | 2.003 | 229.3 | 228.9 |
| 1529 | 1.965 | 229.2 | 228.9 |
| 1559 | 1.929 | 229.2 | 228.9 |
| 1589 | 1.893 | 229.2 | 228.9 |
| 1619 | 1.860 | 229.2 | 228.9 |
| Infinite→0.495 | | | |

*Printout from the Hewlett-Packard Unit
**Pressure was converted to millivolts for readout purposes by the Hewlett-Packard Unit To calibrate the capillary 28, it is isolated from process line 11 by closing valve 16, the calibration vessel or cylinder 22 is slightly pressurized to about 1700 torr, cylinder 22 is isolated from the pressure source by closing valve 25, and the pressure at the entrance of the capillary vs time is measured over a 10 minute period as the calibration gas sample bleeds through it. The pressure vs time data is fitted by regression analysis to an equation, such as one of the type:

$$t = A + B/P + C/P^2 \qquad \text{Equation 1}$$

where t=time in minutes, P=pressure in torr, and A,B,C, are fitted coefficients of regression. If one wishes to enhance accuracy, additional terms may be added to this equation, such as $+D/P^3$, $+E/P^4$, ..., and/or $+F/\log P$, $+G/\log P^2$, ..., and the like.

The flow rate (Flow) through the capillary in normal cm$^3$/min (i.e., at 760 torr and 21° C.) is given by the equation:

$$\text{Flow} = \frac{(dP/dt)(92.02 \text{ cm}^3)(294.16)}{(760 \text{ torr})(273.16 + T)} \qquad \text{Equation 2}$$

where 92.02 cm³ is the value for V, the calibration volume in cc, and T is the temperature of the capillary 28 in °C.

The pressure vs time data curve provides calibration data throughout the complete range of recorded pressures via differentiation of Equation 1:

$$dt = (-BP^{-2} - 2CP^{-3}) dP \quad \text{Equation 3}$$

which yields:

$$dP/dt = P^3/(-BP - 2C)$$

When Equation 3 is substituted into Equation 2, the calibrated flow of the capillary can be obtained over a wide range of process-line pressures by one calibration run (in this case, 1140-380 torr).

The equations usually represent the pressure data to better than 0.1% as shown by the comparisons in Table 6 for selected data in Run 16. Table 7 reports the constants for the equations derived from triplicate runs at three different temperatures, nominally 230, 266, and 292° C. The first derivative of each equation represents the rate of change in pressure at any pressure. The reciprocals of the first derivatives for these equations are reported in Table 8 along with the means and 95% confidence intervals at four arbitrarily chosen pressures (520, 640, 760, and 880 torr; nominally 10.0, 12.4, 14.7 and 17.0 psia). The physical significance of the negative sign is that the pressures are decreasing. Reciprocals have been calculated because the form of the equation yields time/pressure whereas pressure/time is sought.

TABLE 6

Selected Data from Rune 16*

| Time (min) | Experimental Pressure** (torr) | Calculated Pressure (torr) | Difference Calc-Expt/Expt (%) |
|---|---|---|---|
| 1.48 | 1170.16 | 1171.08 | 0.078 |
| 1.98 | 1056.89 | 1057.22 | 0.031 |
| 2.48 | 963.71 | 963.59 | −0.012 |
| 2.98 | 885.48 | 885.26 | −0.026 |
| 3.48 | 818.97 | 818.74 | −0.028 |
| 3.98 | 761.78 | 761.56 | −0.029 |
| 4.48 | 712.11 | 711.88 | −0.032 |
| 4.98 | 668.43 | 668.32 | −0.017 |
| 5.48 | 629.88 | 629.80 | −0.012 |
| 5.98 | 595.51 | 595.51 | −0.000 |
| 6.48 | 564.73 | 564.77 | 0.007 |
| 6.98 | 537.04 | 537.08 | 0.008 |
| 7.48 | 511.90 | 511.99 | 0.017 |
| 7.98 | 489.08 | 489.15 | 0.015 |
| 8.48 | 468.22 | 468.28 | 0.013 |
| 8.98 | 449.07 | 449.13 | 0.014 |
| 9.48 | 431.46 | 431.50 | 0.009 |
| 9.98 | 415.22 | 415.21 | −0.002 |
| 10.48 | 400.08 | 400.11 | 0.007 |
| 10.98 | 386.15 | 386.09 | −0.016 |
| 11.48 | 373.07 | 373.02 | −0.013 |

*The selected data is subsequently cited as Run 16a, etc.
**Calculated using the equation:
P(torr) = 85.48795 × (P(mv) + 0.320)
This is an empirical formula for the specific transducer used.

TABLE 7

Equations Representing the Decrease in Pressure
Equation:[a] t = A + B/P + C/p²

| Run | Capillary Temperature (°C.)[b] | Std Volume Temperature (°C.)[b] | Regression Coefficients A | B | C |
|---|---|---|---|---|---|
| 14a | 232.9 ± 1.7 | 233.1 ± 0.2 | −3.118282 | 5296.417 | 48805.90 |
| 15a | 229.7 ± 0.1 | 229.5 ± 0.1 | −3.147249 | 5388.415 | 25334.36 |
| 16a | 229.8 ± 0.1 | 229.1 ± 0.1 | −3.141977 | 5398.403 | 21307.03 |
| 17a | 266.4 ± 0.1 | 265.4 ± 0.4 | −3.288292 | 5629.372 | 31801.88 |
| 18a | 266.1 ± 0.2 | 266.2 ± 0.2 | −3.324015 | 5634.137 | 27868.16 |
| 19a | 265.6 ± 1.1 | 267.0 ± 0.4 | −3.284299 | 5606.137 | 27436.95 |
| 20a | 292.8 ± 0.1 | 291.8 ± 0.3 | −3.361382 | 5833.209 | 24612.92 |
| 21a | 292.0 ± 0.1 | 291.2 ± 0.2 | −3.379733 | 5778.236 | 35003.13 |
| 22a | 292.4 ± 0.1 | 291.3 ± 0.2 | −3.380060 | 5797.902 | 31993.51 |

[a]Time, t, is in minutes; pressure, P, is in torr. The coefficient of determination is 1.0000 in all cases.
[b]Temperatures are reported as mean of the spread ± spread/2.

TABLE 8

Reciprocal of the First Derivatives of the Pressure Equations

| Run | Pressure (torr) 520 | 640 | 760 | 880 |
|---|---|---|---|---|
| 14a | −49.31 | −75.17 | −106.47 | −143.21 |
| 15a | −49.29 | −74.91 | −105.88 | −142.20 |
| 16a | −49.34 | −74.95 | −105.90 | −142.17 |
| Mean | −49.312 | −75.011 | −106.084 | −142.528 |
| ±95% CL | 0.052 | 0.281 | 0.684 | 1.204 |
| ±95% CL (%) | 0.11 | 0.37 | 0.64 | 0.84 |
| 17a | −47.01 | −71.50 | −101.10 | −135.82 |
| 18a | −47.10 | −71.59 | −101.20 | −135.92 |
| 19a | −47.34 | −71.96 | −101.72 | −136.62 |
| Mean | −47.150 | −71.685 | −101.341 | −136.118 |
| ±95% CL | 0.348 | 0.496 | 0.673 | 0.878 |
| ±95% CL (%) | 0.74 | 0.69 | 0.66 | 0.65 |
| 20a | −45.62 | −69.30 | −97.93 | −131.50 |
| 21a | −45.73 | −69.57 | −98.39 | −132.20 |
| 22a | −45.67 | −69.45 | −98.20 | −131.91 |
| Mean | −45.671 | −69.441 | −98.174 | −131.869 |
| ±95% CL | 0.112 | 0.269 | 0.469 | 0.718 |
| ±95% CL (%) | 0.26 | 0.39 | 0.48 | 0.54 |

Using the size of the known calibration volume (92.02 cc), the absolute flow rate at any pressure may be calculated for that temperature. At 230° C. and 640 torr total pressure, for example, the calculated absolute flow rate using this technique is 5.30±0.03 nccm (normal cubic centimeters per minute, i.e., at 760 torr and 21.0° C.) The experimental flow rate for this capillary as previously determined was 5.15±0.04 nccm at 231±2° C. and 639.7 torr in Example A1. A full comparison of the calculated flow rates is presented in Table 9. The 95% confidence limits for means of the triplicate determinations of the flow rates was less than 1% of the flow rate in all cases.

These data provide experimental verification that the flow rate under the conditions described depends almost entirely on the upstream pressure squared as predicted by theory. Specifically, at 292° C., the mean flow rate at 520 torr is 2.876±0.011 nccm. Hence, (2.876±0.011)×(880/520)² = 8.237±0.032@880 torr.

This differs from the observed value at 880 torr, 8.305±0.056, by less than one percent (−0.82%).

A similar comparison of the theoretical changes in flow rate as a result of changes in gas temperature alone shows less agreement.

TABLE 9
Capillary Flow Rates at Selected Pressures

Equation[a]: $\text{Rate (nccm)} = \dfrac{\text{Slope} \times 92.02 \times 294.16}{760 \times [273.16 + t\,(\text{cyl})]}$

| Run | Rate (nccm) at Pressure (torr) | | | |
|---|---|---|---|---|
| | 520 | 640 | 760 | 880 |
| 14a | 3.469 | 5.288 | 7.491 | 10.075 |
| 15a | 3.493 | 5.308 | 7.503 | 10.076 |
| 16a | 3.499 | 5.314 | 7.514 | 10.079 |
| Mean | 3.487 | 5.303 | 7.503 | 10.077 |
| ± 95% CL | 0.032 | 0.028 | 0.023 | 0.004 |
| ± 95% CL (%) | 0.92 | 0.52 | 0.31 | 0.04 |
| 17a | 3.109 | 4.728 | 6.686 | 8.982 |
| 18a | 3.111 | 4.727 | 6.682 | 8.976 |
| 19a | 3.122 | 4.745 | 6.707 | 9.008 |
| Mean | 3.114 | 4.733 | 6.692 | 8.989 |
| ± 95% CL | 0.014 | 0.021 | 0.027 | 0.035 |
| ± 95% CL (%) | 0.46 | 0.43 | 0.41 | 0.38 |
| 20a | 2.871 | 4.361 | 6.163 | 8.276 |
| 21a | 2.882 | 4.384 | 6.200 | 8.331 |
| 22a | 2.876 | 4.374 | 6.184 | 8.307 |
| Mean | 2.876 | 4.373 | 6.182 | 8.305 |
| ± 95% CL | 0.011 | 0.023 | 0.038 | 0.056 |
| ± 95% CL (%) | 0.39 | 0.53 | 0.61 | 0.67 |

[a] nccm = normal cubic centimeters per minute, i.e., at 760 torr and 21.0° C.

Specifically, at 520 torr, the mean flow rate at 230° C. is 3.487±0.032 nccm. Hence, $$(3.487 \pm 0.032) \times 503/565 = 3.104 \pm 0.028 \, @ \, 292° \text{ C.}$$

This differs from the observed value at 292° C., 2.876±0.011, by about eight percent (+7.93%).

These deviations from theory illustrate why in-situ calibration of process monitors is the best method for attaining and maintaining high accuracy. The modification to the high temperature process stream nitrogen oxide measurement system described permits in-situ calibration of the flow restricting capillary or orifice. The accuracy of this flow calibration is as good as other available methods. The time required for such a calibration or verification of calibration is less than 20 minutes under operating conditions. Simultaneous use of a calibration gas routes both the calibration gas and the sample through the capillary, thus allaying any concern over possible sample fractionation which could cause inaccuracies.

The calibration invention as described was operated at nominal temperatures of 230, 266, and 292° C. There is no practical reason that the principal cannot be applied at higher temperatures or at lower temperatures, even subambient temperatures, if the materials of construction and the calibration gases are compatible with the proposed use.

In this particular calibration example, a Mini-Eductor was the vacuum source. Alternative vacuum sources could, of course, be used which would permit application of the principal at lower pressures.

The volume of the standard cylinder 22 was calculated at ambient temperatures. The corrected volume, after taking into account the coefficient of thermal expansion of the stainless steels, can be applied to utilize a more accurate volume in the calculations.

Those skilled in the art will recognize that the data acquisition system could be a more "user friendly" version which could reduce the raw data directly to a usable form or which could utilize the calibration directly in performing subsequent calculations. A programed computer or a microprocessor could be utilized.

The absolute pressure transmitter in the example was removed from the heated zone and insulated from temperature fluctuations. This unheated volume was about 1 cc, which is quite small compared to the total volume of about 92 cc. In a system which could condense potentially explosive compounds, either a pressure transducer operable at high temperature or a flexible, transmitting cable filled with an inert fluid such as a high temperature silicone oil could be used. This action would assure that all process gases remained heated during operation of the invention. This alternative would be useful, for example, in situations where gaseous nitrogen oxides and ammonia might be cooled below about 210° C., possibly depositing ammonium nitrate.

Accordingly, therefore, in light of the foregoing disclosure, further alternative embodiments of the inventive method and apparatus for high temperature $NO_x$ determination and flow calibration will undoubtedly suggest themselves to those skilled in the art. It is thus intended that the disclosure be taken as illustrative only, and that it not be construed in any limiting sense. Modifications and variations may be resorted to without departing from the spirit and the scope of this invention, and such modifications and variations are considered to be within the purview and the scope of the appended claims.

What is claimed is:

1. Fluid sampling apparatus which comprises:
   a. a fluid inlet conduit including means for fluid connection to a source containing fluid to be sampled;
   b. an aspirator device having a suction inlet opening for the fluid to be sampled, a motive fluid inlet opening, and an exit opening;
   c. a restrictive flow conduit in fluid communication with said inlet conduit and with the section inlet opening of said aspirator device;
   d. a motive fluid inlet conduit in fluid communication with the motive fluid inlet opening of said aspirator device, said motive fluid inlet conduit including means for connection to a source of motive fluid for creating a dilute mixture of motive fluid and sample fluid, said motive fluid inlet capable of providing variable dilution ratios of sample fluid to motive fluid;
   e. first heating means at said restrictive flow conduit for heating a sample of fluid passing therethrough;
   f. second heating means at said motive fluid inlet conduit for heating motive fluid passing therethrough;
   g. a discharge conduit in fluid communication with said aspirator device exit opening for discharging the diluted mixture of motive fluid and sample fluid.

2. Fluid sampling apparatus according to claim 1 wherein said motive fluid inlet conduit further includes a mass flow controller and a flow control valve, the mass flow controller capable of sending a signal to the flow control valve and controlling the amount of dilution of the sample fluid to prevent precipitation from the dilute mixture of sample fluid in motive fluid.

3. Fluid sampling apparatus according to claim 1 wherein said discharge conduit further includes means for withdrawing a portion of discharged fluid mixture for transmission to sample analysis apparatus.

4. Fluid sampling apparatus according to claim 1 further including a fluid calibration vessel of known volume having a temperature sensor and in fluid communication with said fluid inlet conduit upstream of said restrictive flow conduit.

5. Fluid sampling apparatus according to claim 4 further including a valve in said fluid inlet conduit for isolating said fluid source to be sampled, and a valve at said calibration vessel for isolating said vessel from said fluid inlet conduit and from said restrictive flow conduit.

6. Fluid sampling apparatus according to claim 1 wherein said restrictive flow conduit comprises a capillary.

7. Fluid sampling apparatus according to claim 1 wherein said restrictive flow conduit comprises a restriction orifice.

8. Fluid sampling apparatus according to claim 1 further including an external housing defining an encompassing chamber.

9. Fluid sampling apparatus according to claim 8 further including heating means for heating said chamber.

10. Fluid sampling apparatus, suitable for sampling a high temperature gas for nitrogen oxide measurement, which comprises:
   a. an inlet conduit including means for connection to a high temperature gas source to be sampled;
   b. an aspirator device having a suction inlet opening, a motive gas inlet opening, and an exit opening for discharging a gas mixture of motive gas and sample gas;
   c. a restrictive flow conduit in fluid communication with said inlet conduit and with the suction inlet opening of said aspirator device;
   d. a motive gas inlet conduit in fluid communication with the motive gas inlet opening of said aspirator device, said motive gas inlet conduit including means for connection to a source of motive gas for creating a dilute mixture of motive gas and sample gas, said motive gas inlet capable of providing variable dilution ratios of sample gas to motive gas;
   e. first heating means at said restrictive flow conduit, said first heating means having the capacity to maintain a gas sample passing through said restrictive flow conduit at a temperature not less than the high temperature of said gas source;
   f. second heating means at said motive gas inlet conduit for heating motive gas passing therethrough; and
   g. a discharge conduit in fluid communication with said aspirator device exit opening for discharging the diluted mixture of motive gas and sample gas.

11. Fluid sampling apparatus according to claim 10 wherein said motive gas inlet conduit further includes a mass flow controller and a flow control valve, the flow controller capable of sending a signal to the flow control valve to provide that said mixture will contain a ratio of motive gas to sample gas of at least 1,000,000,000:1 to prevent the precipitation of ammonium nitrate from the diluted mixture of sample gas in motive gas.

12. Fluid sampling apparatus according to claim 10 wherein said discharge conduit further includes means for withdrawing a portion of discharged fluid mixture for transmission to sample analysis apparatus.

13. Fluid sampling apparatus according to claim 10 further including a calibration vessel of known volume having a temperature sensor for isolating said vessel from said inlet conduit and from said restrictive flow conduit.

14. Fluid sampling apparatus according to claim 13 further including a valve in said inlet conduit for isolating said gas source to be sampled, and a valve at said calibration vessel for isolating said vessel from said inlet conduit and from said restrictive flow conduit.

15. Fluid sampling apparatus according to claim 10 wherein said restrictive flow conduit comprises a capillary.

16. Fluid sampling apparatus according to claim 10 wherein said restrictive flow conduit comprises a restriction orifice.

17. Fluid sampling apparatus according to claim 10 further including an external housing defining an encompassing chamber.

18. Fluid sampling apparatus according to claim 17 further including heating means for heating said chamber.

19. Method for determining nitrogen oxide content in a high temperature gas, which comprises,
   a. withdrawing a sample portion of a high temperature gas containing nitrogen oxide from a high temperature gas source to be analyzed;
   b. passing said sample portion through a restrictive flow conduit;
   c. heating said restrictive flow conduit to maintain said sample portion flowing therethrough at an elevated temperature at least as great as the temperature of said high temperature gas source to thereby provide that deposition of ammonium nitrate within said restrictive flow conduit cannot occur;
   d. drawing said sample portion from said restrictive flow conduit into the suction side of an aspirator device;
   e. passing a flow of motive gas to said aspirator device under conditions sufficient to aspirate said heated sample portion from said restrictive flow conduit and produce a dilute mixture of said sample portion in motive gas;
   f. passing at least a portion of said dilute mixture at a temperature reduced from said elevated temperature from said aspirator device to analytical means capable of detecting at least nitric oxide; and,
   g. adjusting the flow of motive gas to vary the dilution ratio in the dilute mixture and to prevent deposition of ammonium nitrate from said mixture at the reduced temperature.

20. Method according to claim 19 wherein said reduced temperature is not less than ambient temperature.

21. Method according to claim 19 wherein said motive gas is heated to a temperature at least as great as the temperature of said high temperature gas source before being passed into said aspirator device.

22. Method according to claim 19 wherein said aspirator device is maintained at a temperature at least as great as the temperature of said high temperature gas source.

23. Method according to claim 19 further including the steps of determining the flow rate of sample portion through said restrictive flow conduit, determining the flow rate of motive gas to said aspirator device, determining the dilution factor of sample portion in said dilute mixture from said flow rates, determining at least the nitric oxide content of said mixture by said analytical means, and multiplying said nitric oxide content of said mixture by said dilution factor to determine the concentration of nitric oxide in said high temperate gas source.

24. Method according to claim 19 wherein said analytical means is capable of determining the amount of nitrogen species selected from the group consisting of nitric oxide, nitrogen dioxide, ammonia, and mixtures thereof contained in said dilute mixture of sample portion and motive gas.

25. Method according to claim 24 further including the steps of determining the flow rate of sample portion through said restrictive flow conduit, determining the flow rate of motive gas to said aspirator device, determining the dilution factor of sample portion in said dilute mixture from said flow rates, determining the content of said nitrogen species in said dilute mixture by said analytical means, and multiplying said contents in said mixture by said dilution factor to determine the concentration of detected nitrogen species in said high temperature gas source.

26. Method according to claim 19 wherein said restrictive flow conduit comprises a capillary.

27. Method according to claim 19 wherein said restrictive flow conduit comprises a restriction orifice.

28. Method according to claim 19 wherein said restrictive flow conduit is periodically calibrated by the steps of:
   a. bringing said restrictive flow conduit and a calibration vessel of known volume to a desired operating temperature for calibration, said desired operating temperature being maintained at not less than the temperature of said high temperature gas source;
   b. pressurizing said calibration vessel with a calibration gas to an elevated pressure above the normal pressure of said sample portion, and isolating the calibration gas in said calibration vessel from the calibration gas source;
   c. stopping the flow of said sample portion through said restrictive flow conduit;
   d. initiating the flow of calibration gas from said calibration vessel to said restrictive flow conduit;
   e. measuring and recording times, pressures, and temperatures of the inlet side of said restrictive flow conduit as the volume of calibration gas is evacuated from said calibration vessel through said restrictive flow conduit and into said aspirator device by motive gas to produce a dilute mixture of calibration gas in motive gas;
   f. applying a multiple regression analysis technique to accurately fit the recorded data points to an equation of the type $t = A + B/P + C/P^2$ where t=time in minutes, P=pressure in torr, and A, B, C are fitted coefficients of regression;
   g. calculating the first derivative of said equation at pressures for which calibration is desired, to yield the equation $dP/dt = P^3/(-BP - 2C)$; and, h. applying values of dP/dt at specific pressures to determine volume flow rate at said specific pressures according to the equation $$\text{Flow} = \frac{(dP/dt)\,(V)\,(294.16)}{(760)\,(273.16 + T)}$$

where Flow is normal cubic centimeters per minute at 760 torr and 2120 C., V is the calibration volume in $cm^3$ at 760 torr and 21° C., and T is the temperature of said restrictive flow conduit in °C.

29. Method according to claim 28 wherein said calibration gas contains a known content of at least one nitrogen species selected from the group consisting of nitric oxide, nitrogen dioxide, and ammonia, and a portion of said dilute mixture of calibration gas in motive gas is passed to said analytical means for detection of said nitrogen species as a calibration check for said analytical means.

30. Method according to claim 19 wherein said analytical means is periodically calibrated by the steps of:
   a. bringing said restrictive flow conduit and an input source of calibration gas to a desired operating temperature for calibration, said desired operating temperature being maintained at not less than the temperature of said high temperature gas source;
   b. passing a calibration gas, having a known content of at least one nitrogen species selected from the group consisting of nitric oxide, nitrogen dioxide, and ammonia, from said input source to said restrictive flow conduit at an elevated pressure above the normal pressure of said sample portion to thereby stop the flow of said sample portion into said restrictive flow conduit;
   c. passing said calibration gas from said restrictive flow conduit to said suction side of said aspirator device;
   d. discharging from said aspirator device a dilute mixture of calibration gas in said motive gas at a dilution of calibration gas to provide that deposition of ammonium nitrate from said dilute calibration gas mixture cannot occur at reduced temperature; and,
   e. passing at least a portion of said dilute calibration gas mixture at reduced temperature to said analytical means for detection of said nitrogen species as a calibration check for said analytical means.

* * * * *